US008986273B2

(12) United States Patent
Mercer et al.

(10) Patent No.: US 8,986,273 B2
(45) Date of Patent: Mar. 24, 2015

(54) ABSORBENT PERSONAL CARE ARTICLE HAVING INTERMESHING FLAPS

(71) Applicant: Kimberly-Clark Worldwide, Inc., Neenah, WI (US)

(72) Inventors: Luciana V. Mercer, São Paulo-SP (BR); Rogério B. Bastos, Guaiba (BR); Paula C. Winkel, Chilton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 327 days.

(21) Appl. No.: 13/662,129

(22) Filed: Oct. 26, 2012

(65) Prior Publication Data

US 2013/0123731 A1    May 16, 2013

Related U.S. Application Data

(60) Provisional application No. 61/558,259, filed on Nov. 10, 2011.

(51) Int. Cl.
| | |
|---|---|
| *A61F 13/47* | (2006.01) |
| *A61F 13/476* | (2006.01) |
| *A61F 13/56* | (2006.01) |

(52) U.S. Cl.
CPC .................................. *A61F 13/5616* (2013.01)
USPC ................................ 604/385.04; 604/385.03

(58) Field of Classification Search
CPC ... A61F 13/476; A61F 13/5616; A61F 13/05; A61F 2013/586; A61F 2013/587; A61F 2013/588
USPC ............ 604/308, 385.04, 386, 387, 389, 391; 602/52, 54, 62; D24/125, 189
See application file for complete search history.

(56) References Cited

U.S. PATENT DOCUMENTS

| | | |
|---|---|---|
| 3,881,490 A | 5/1975 | Whitehead et al. |
| 3,913,580 A | 10/1975 | Ginocchio |
| 4,059,114 A | 11/1977 | Richards |
| 4,285,343 A | 8/1981 | McNair |
| 4,337,772 A | 7/1982 | Roeder |
| 4,376,799 A | 3/1983 | Tusim |
| 4,397,644 A | 8/1983 | Matthews et al. |

(Continued)

FOREIGN PATENT DOCUMENTS

| | | |
|---|---|---|
| EP | 0607986 A1 | 7/1994 |
| EP | 0511905 B1 | 8/1995 |

(Continued)

*Primary Examiner* — Tan-Uyen (Jackie) T Ho
*Assistant Examiner* — Kathryn E Ditmer

(57) ABSTRACT

An absorbent personal care article, such as a sanitary napkin or incontinence pad, having a longitudinal centerline and a transverse centerline and including a pair of opposed first and second wings extending along the longitudinal sides of the article. The first wing includes two or more peaks with furrows therebetween and the second wing includes one or more peaks. The peaks of the first and second wings are sized and positioned on the article such that when folded under the article and around the wearer's undergarments, the peak of the second wing extends across the longitudinal centerline of the article and into the furrow of the first wing. The intermeshing wings help wearer's properly don the articles, improve the attachment of the article to the wearer's garment and/or reduce unwanted twisting or bunching of the article during use.

20 Claims, 6 Drawing Sheets

(56) References Cited

U.S. PATENT DOCUMENTS

| | | |
|---|---|---|
| 4,556,146 A | 12/1985 | Swanson et al. |
| 4,578,069 A | 3/1986 | Whitehead et al. |
| 4,589,876 A | 5/1986 | Van Tilburg |
| 4,610,678 A | 9/1986 | Weisman et al. |
| 4,629,643 A | 12/1986 | Curro et al. |
| 4,781,710 A | 11/1988 | Megison et al. |
| 4,862,574 A | 9/1989 | Seidy |
| 5,087,254 A | 2/1992 | Davis et al. |
| 5,188,625 A | 2/1993 | Van Iten et al. |
| 5,342,647 A | 8/1994 | Heindel et al. |
| 5,382,400 A | 1/1995 | Pike et al. |
| 5,401,268 A | 3/1995 | Rodier |
| D365,147 S | 12/1995 | Hamel |
| 5,533,991 A | 7/1996 | Kirby et al. |
| 5,580,411 A | 12/1996 | Nease et al. |
| 5,626,572 A | 5/1997 | Ahr et al. |
| 5,695,849 A | 12/1997 | Shawver et al. |
| 5,865,777 A * | 2/1999 | Detty ........................ 602/26 |
| 6,060,636 A | 5/2000 | Yahiaoui et al. |
| 6,075,179 A | 6/2000 | McCormack et al. |
| 6,171,432 B1 | 1/2001 | Brisebois et al. |
| 6,376,095 B1 | 4/2002 | Cheung et al. |
| 6,410,823 B1 | 6/2002 | Daley et al. |
| 6,585,710 B1 | 7/2003 | Brisebois |
| 6,610,903 B1 | 8/2003 | Latimer et al. |
| 6,652,701 B1 | 11/2003 | Boulanger |
| D504,509 S | 4/2005 | Lavash |
| 6,964,655 B2 | 11/2005 | Killeen et al. |
| 7,070,672 B2 | 7/2006 | Alcantara et al. |
| D543,622 S | 5/2007 | Lash et al. |
| D543,623 S | 5/2007 | Lash et al. |
| D561,895 S | 2/2008 | Sergeant |
| 7,358,282 B2 | 4/2008 | Krueger et al. |
| D594,973 S | 6/2009 | Francoeur |
| 7,686,790 B2 | 3/2010 | Rasmussen et al. |
| 7,749,182 B2 * | 7/2010 | Gramza et al. ................ 602/26 |
| 7,780,615 B1 * | 8/2010 | Shesol ........................ 602/22 |
| D626,219 S | 10/2010 | Rubio |
| 7,811,271 B2 | 10/2010 | Digiacomantonio et al. |
| D635,250 S | 3/2011 | Rubio |
| D635,251 S | 3/2011 | Rubio |
| D635,252 S | 3/2011 | Rubio |
| 2003/0087056 A1 | 5/2003 | Ducker et al. |
| 2003/0208177 A1 | 11/2003 | D'Alessio et al. |
| 2004/0040650 A1 | 3/2004 | Venturino et al. |
| 2004/0068244 A1 | 4/2004 | Salone et al. |
| 2004/0133197 A1 | 7/2004 | Steger et al. |
| 2004/0138636 A1 | 7/2004 | Cardin et al. |
| 2005/0124959 A1 | 6/2005 | Alcantara et al. |
| 2005/0182374 A1 | 8/2005 | Zander et al. |
| 2005/0283131 A1 | 12/2005 | Zander et al. |
| 2007/0000987 A1 * | 1/2007 | Karlsson ........................ 229/151 |
| 2007/0073255 A1 | 3/2007 | Thomas et al. |
| 2008/0276439 A1 | 11/2008 | Andrews et al. |
| 2010/0071843 A1 | 3/2010 | Gaston et al. |
| 2010/0087793 A1 | 4/2010 | Magnusson et al. |
| 2010/0174260 A1 | 7/2010 | Di Luccio et al. |
| 2010/0305539 A1 | 12/2010 | Odoi |
| 2010/0312215 A1 | 12/2010 | Odoi |

FOREIGN PATENT DOCUMENTS

| | | |
|---|---|---|
| EP | 0 769 284 A1 | 4/1997 |
| EP | 0 982 017 A2 | 3/2000 |
| EP | 1208823 A1 | 5/2002 |
| EP | 1138294 B1 | 10/2004 |
| FR | 2644694 A1 | 9/1990 |
| GB | 1 349 962 A | 4/1974 |
| JP | 2010-227241 A | 10/2010 |
| KR | 20-2010-0001127 U | 2/2010 |
| KR | 2010-0001127 U | 2/2010 |
| WO | WO 91/16873 A1 | 11/1991 |
| WO | WO 9116873 A1 * | 11/1991 |
| WO | WO 96/38110 A1 | 12/1996 |
| WO | WO 9638110 A1 * | 12/1996 |
| WO | WO 97/40804 | 11/1997 |
| WO | WO 98/06367 A1 | 2/1998 |
| WO | WO 03/015682 | 2/2003 |
| WO | WO 03/015684 | 2/2003 |
| WO | WO 2004/105670 A1 | 12/2004 |
| WO | WO 2004105670 A1 * | 12/2004 |
| WO | WO 2005/079723 A1 | 9/2005 |

* cited by examiner

ABSORBENT PERSONAL CARE ARTICLE HAVING INTERMESHING FLAPS

PRIORITY

This non-provisional application claims priority of Provisional Application No. 61/558,259, filed on Nov. 10, 2011. The entirety of Application No. 61/558,259 is incorporated herein by reference.

FIELD OF THE INVENTION

The present invention relates to fastening systems for absorbent personal care articles. More particularly, it relates to absorbent personal care articles having foldable wings or flaps that can be employed to properly position and attach the absorbent articles to undergarments or other articles of clothing.

BACKGROUND

Absorbent personal care articles such as sanitary napkins, panty liners and incontinence pads commonly utilize a pair of wings or flaps which are used to help secure the article in place to the wearer's undergarments. Generally, the wings are folded around the outside of the wearer's undergarment and attach to the outside of the undergarment via adhesive or other fastening means. Once secured to the undergarment the wings help reduce the likelihood that the article will become dislodged and move out of position. Examples of such foldable wing fasteners are shown and described in U.S. Pat. No. 4,589,876 Van Tilberg; EP0511905B1 Pigneul; U.S. Pat. No. 5,401,268 Rodier; and EP1208823A1 Hohmann.

However, while wings of various size and shape have previously been used, there remain a number of drawbacks to these designs. First, many wings do not adequately prevent the article from bunching or twisting due to the stresses imparted on the article as the wearer moves. Second, misapplication of the article to the undergarment can also greatly increase the risk of leakage. In this regard, it can be difficult for wearers to place conventional wings properly onto their undergarment and when the wings are improperly fastened the absorbent article can be bunched or partially twisted as donned or more easily become twisted or bunched with the wearer's movement. Twisting of the article and/or the deformation of the article when worn can result in the article being at an angle relative to the wearer as opposed to being perpendicular to or flat against the wearer. When the article is sidewardly angled to the wearer the ability of the article to take in and absorb fluids can be reduced to an extent such that the article functions significantly less effectively than desired. Further, bunching of the article results in the article covering considerably less area under the vaginal region than desired. Thus, such unwanted twisting and bunching of the article can result in increased frequency of leakage and staining of the wearer's garments.

Thus, there exists a continued need for an absorbent personal care article having foldable wings that assist the wearer with proper placement and donning of the article.

There further exists a need for such an article wherein the foldable wings also help maintain the article in an uncontorted and/or generally flap shape in order to minimize the incidence of leakage.

SUMMARY OF THE INVENTION

The present invention addresses problems experienced with the flap designs of the prior art by providing an absorbent personal care article including (i) a left flap having first and second peaks and a furrow positioned there between, and (ii) a right flap having a first peak. The left and right flaps are positioned on opposed longitudinal sides of the article and sized such that, when the flaps are folded under the article and extended so that they lay flat against the liquid impermeable backsheet, the right flap peak extends across the longitudinal centerline of the article and into the left flap furrow.

In a further aspect of the invention, the left and right flaps can be integrally shaped and sized such that the wings substantially inter-mesh with or conform to one another when folded under and around the article. In still a further embodiment, the left and right flaps may define a space or gap between them along the substantial length of the flaps when the flaps are folded under the article lying flat adjacent the liquid impermeable backsheet. In an alternate embodiment, the left and right flaps can be sized and shaped so as to form one or more discrete areas of overlap when the flaps are folded under and around the article and lay flat against the liquid impermeable backsheet.

In a further aspect of the invention, the left and right flaps may include fasteners located on the garment facing side of the flap peaks such that the fastener extends across the longitudinal centerline of the article and either into the furrow of the opposed flap or over the opposed flap. This may be achieved, in one embodiment, by placing the fastener proximate the outer edges of the flap peaks.

DESCRIPTION OF THE INVENTION

Figure 1:
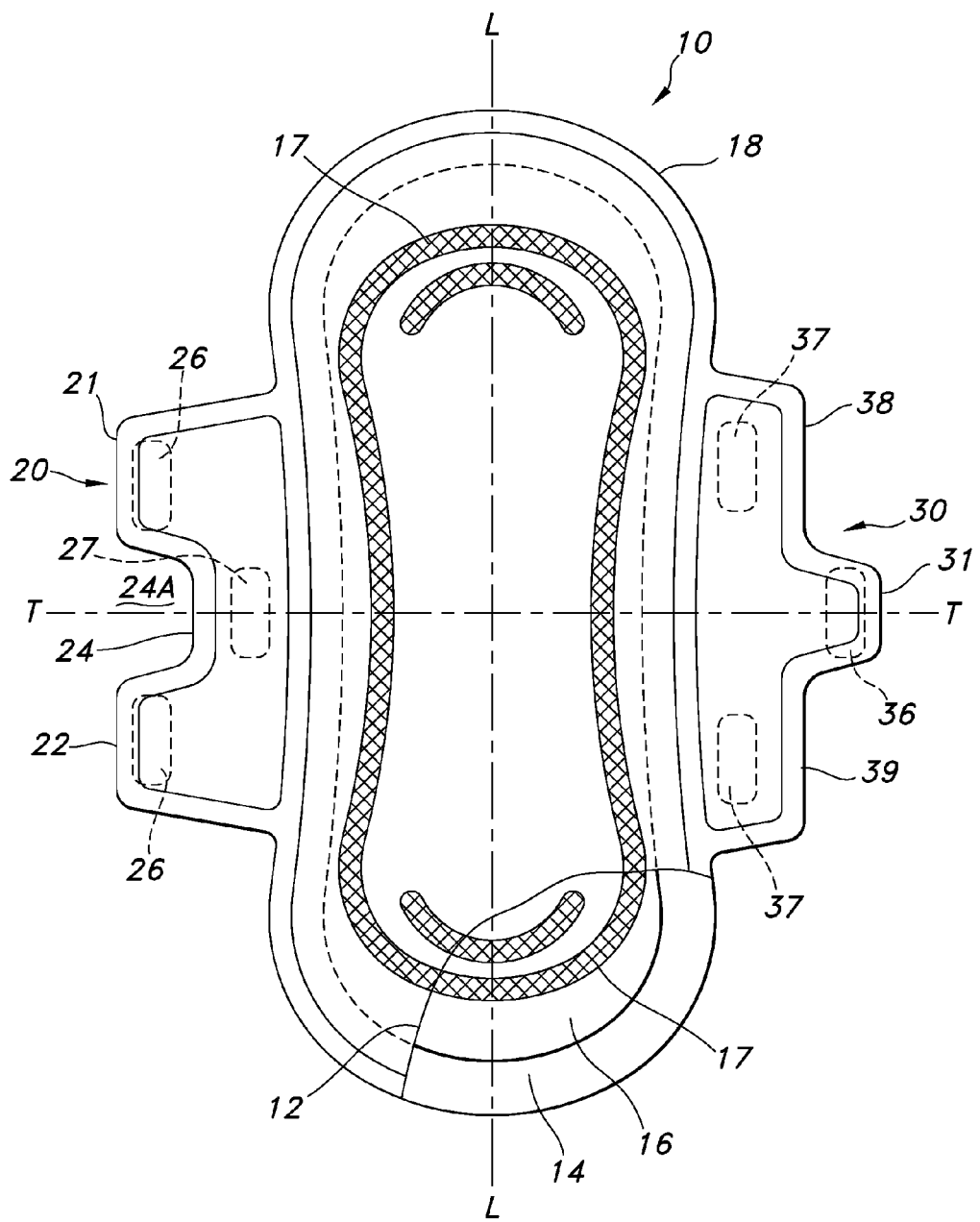
FIG. 1 is a representative partially cut away plan view of one embodiment of a sanitary napkin of the present invention in a flat and unfolded state.
Figure 2:
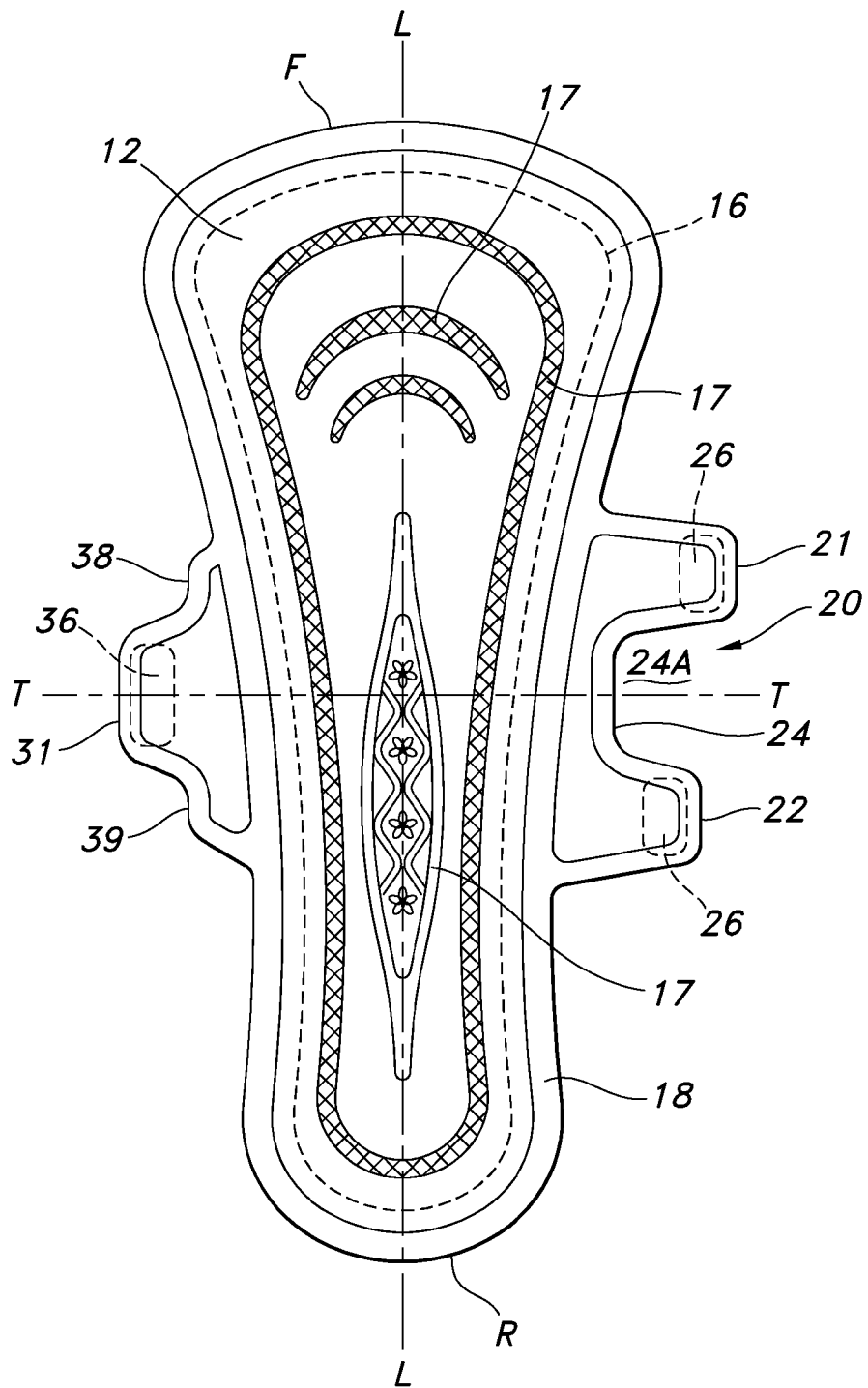
FIG. 2 is a representative plan view of a sanitary napkin of an alternate embodiment of the present invention suitable for use with both traditional and tanga style underwear.

In reference to FIGS. 1 and 2, the drawings show absorbent personal care articles in a flat and unfolded state. Except as otherwise noted, discussion of dimensions of the article and/or the positions of individual components thereof are in reference to the article being in a flat and unfolded state and further, in the event elasticated components are utilized, dimensions are in reference to the article being in an uncontracted state. Further, as used herein, the terms "comprising" or "including" are inclusive or open-ended and do not exclude additional unrecited elements, compositional components, or method steps. Accordingly, the terms "comprising" or "including" encompass the more restrictive terms "consisting essentially of" and "consisting of."

In reference to FIG. 1, an absorbent personal care article 10 is provided comprising a liquid permeable topsheet 12, a liquid impermeable backsheet 14 and an absorbent core 16. The absorbent article 10 has a lengthwise or longitudinal direction and a widthwise or transverse direction. The longitudinal centerline of the article 10 is shown as line "L" and the transverse centerline of the article 10 is shown as line "T". The absorbent article 10 can comprise any one of numerous elongate shapes including, but not limited to, triangular, rectangular, dog-bone and elliptical. In addition, it will often times be desirable for the article to have rounded corners and/or generally convex ends.

The absorbent article desirably has a length between about 80 mm and about 450 mm, and still more desirably a length between about 150 mm to about 250 mm. The absorbent article 10 desirably has a maximum width (excluding the wings) between about 40 and about 160 mm, and still more desirably a maximum width between about 65 mm and about 95 mm.

The absorbent article 10 further includes a first wing 20 and second wing 30 extending from opposite longitudinal sides of the article 10. The first and second wings 20, 30 desirably extend from about 20% to about 75% of the length of the article 10. In a further aspect, the wings desirably have a length, in the longitudinal direction L, of from about 40 mm to about 160 mm, and still more desirably a length from about 95 mm to about 145 mm. The wings can be positioned about the transverse centerline or may be positioned either some distance forward or rear of the transverse centerline as may be desired to better accommodate the particular shape of the article and/or use on a particular style of garment. In addition, while not shown, it is noted that absorbent articles can, if desired, contain more than one set of opposed wings of the present invention.

A portion of the outside surface of the wings 20, 30 include one or more fasteners 26, 36. The fastener will be selected to releasably engage either a garment or an overlapping portion of an opposed wing. Numerous adhesives and mechanical hook-type fasteners that releasably attach to itself or a user's garments are well known in the art and are suitable for use in connection with the present invention. Pressure sensitive adhesives are particularly well suited for use with the present invention. However, in order to protect the adhesive from contamination or drying prior to use, the adhesive is commonly protected by one or more releasable peel strips as is known in the art. A suitable releasable peel strip is a white Kraft paper having a silicone coating on one side so that it can be easily released from the adhesive. In addition, with respect to wing-to-wing attachment, examples of specific mechanical hook, adhesive and other fastening systems include but are not limited to those described in WO03/015682 to Hammonds et al.; WO03/015684 to Hammonds et al. and US20040133179 to Steger et al.

The first wing 20 includes at least a first peak 21 and a second peak 22 and a furrow base 24 spanning the peaks; the inner edges of the first and second peaks 21, 22 and the furrow base 24 define a groove or furrow 24A in the first wing 20. The shapes of the peaks and furrow(s) can vary as desired including both rectilinear and curvilinear configurations. The wing 20 and components thereof are sized such that, when the wing 20 is folded around the underside of the article and the wing 21 lays flat against the backsheet 14, portions of the first and second peaks 21, 22 extend across the longitudinal centerline L whereas the furrow base 24 does not extend across or even to the longitudinal centerline. Thus, the specific dimensions for the wings will be selected in relation to the corresponding width of the absorbent article. In one aspect, the dimension of the peak in the transverse direction may be at least 50% of the width of the adjacent section of the absorbent core. In a further aspect, the distance from the middle of the first peak to the middle of the furrow base 24 is desirably at least about 20 mm and still more desirably between about 20 mm and about 60 mm.

The second wing 30 includes at least a first peak 31 and first and second shoulders 38, 39 positioned on opposite sides of the first peak 31 of the second wing 30. Individual elements of the second wing 30 can have dimensions the same as or similar to those of the first wing 20. However, as discussed in more detail below, desirably the peaks, furrows, and/or shoulders of the first and second wings are shaped so to coincide with one another. The second wing 30 and components thereof are sized such that, when second wing 30 is folded around the underside of the article and lays flat against the backsheet 14, portions of the first peak 31 extend across the longitudinal centerline L whereas the shoulders 38, 39 do not extend across or even to the longitudinal centerline L. The shapes of the peak(s), furrow(s) and/or shoulders can vary as desired including both rectilinear and curvilinear configurations.

The first and second wings 20, 30 are positioned along the longitudinal sides of the article 10 wherein the furrow base 24 of the first wing 20 lies in the same plane as the first peak 31 of the second wing. Stated differently, the first and second wings 20, 30 are positioned along opposed longitudinal sides of the article 10 such that, when the first and second wings 20, 30 are folded around the underside of the article 10 and extended to lay flat against the backsheet 14, the first peak 31 of the second wing 30 extends into the furrow 24A of the first wing 20 (the furrow 24A of the first wing 20 being defined by the peaks 21, 22 and furrow base 24).

Figure 3:
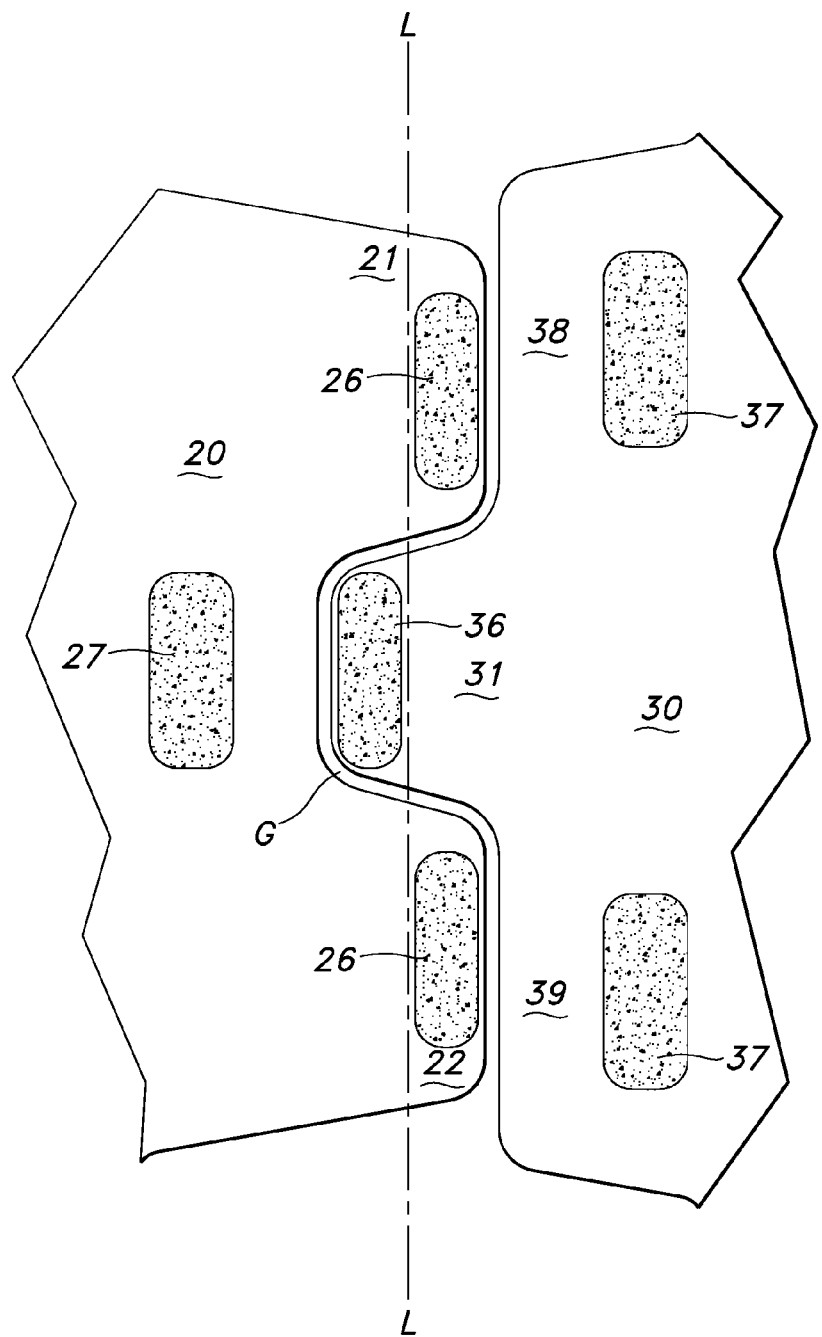
FIGS. 3-6 are enlarged views of individual embodiments of wings of the present invention shown in an inter-meshing relationship as folded directly under the personal care article lying flat against the backsheet.

In one embodiment and in reference to FIG. 3, the first and second wings 20, 30 can be sized and shaped so that, when folded around the underside of the article 10 and extended to lay flat against the backsheet 14, the wings 20, 30 do not overlap thereby leaving a space or gap "G" between them. In the embodiment shown, the wings 20, 30 are sized and shaped so that they substantially intermesh but leave a substantially uniform gap "G" between them when folded around the underside of the article so as to lay flat against the backsheet 14. Desirably in such embodiments the wings leave a gap "G" of less than about 20 mm and still more desirably less than about 15 mm. Thus, in use, the first wing 20 and second wing 30 extend around the crotch portion of the garment, and the first peak 31 of the second wing 30 extends into the furrow 24A of the first wing 20 in a mating relationship. In a further aspect, the first and second peaks 21, 22 of the first wing 20 and the shoulders 38, 39 of the second wing 30 similarly lie in a corresponding relationship having a similar gap between the respective edges. Primary fasteners 26, 36, such as pressure sensitive adhesive, can be positioned adjacent the outer edges of the peaks such that, when the wings 20, 30 are folded under the article so that the wings 20, 30 lie flat against the backsheet 14, the fasteners 26, 36 lie on the opposite side of the longitudinal center line relative to which the wing is attached. The wings may also optionally include secondary fasteners 27, 37 located proximate to outer edges of the furrow base 24, shoulders 38, 39 or base of the peaks 21, 22, 31. The primary fasteners 26, 36 may lie entirely or partially beyond the longitudinal center line when the wings 20, 30 are folded around the underside of the article 10 and lay flat against the backsheet 14. As shown in FIG. 3, when the wings 20, 30 are folded around the underside of the article 10 and lay flat against the backsheet 14, the primary fasteners 26, 36 are positioned entirely on the opposite side of the longitudinal center line "L" relative to the side that the wing extends from.

Figure 4:
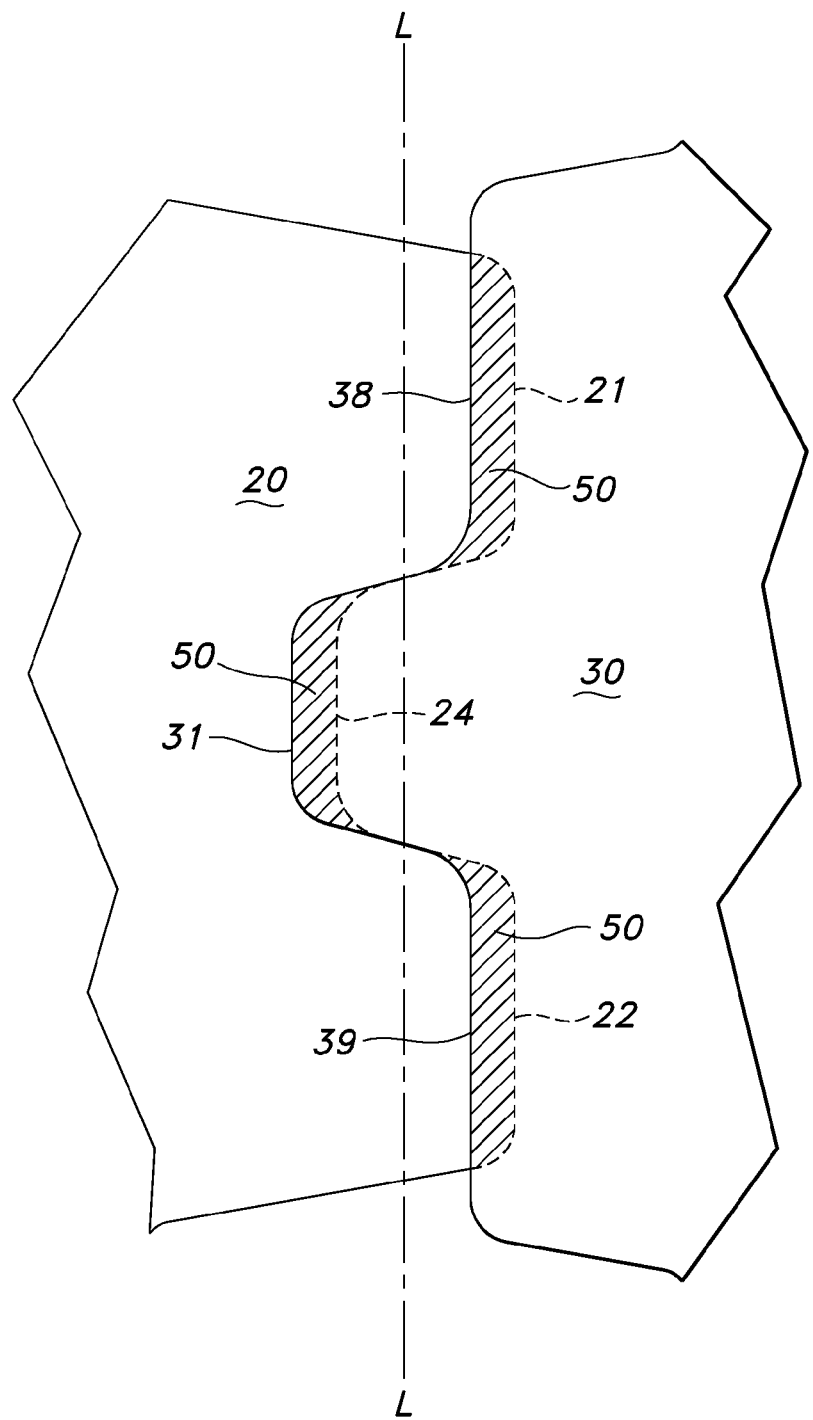
Figure 5:
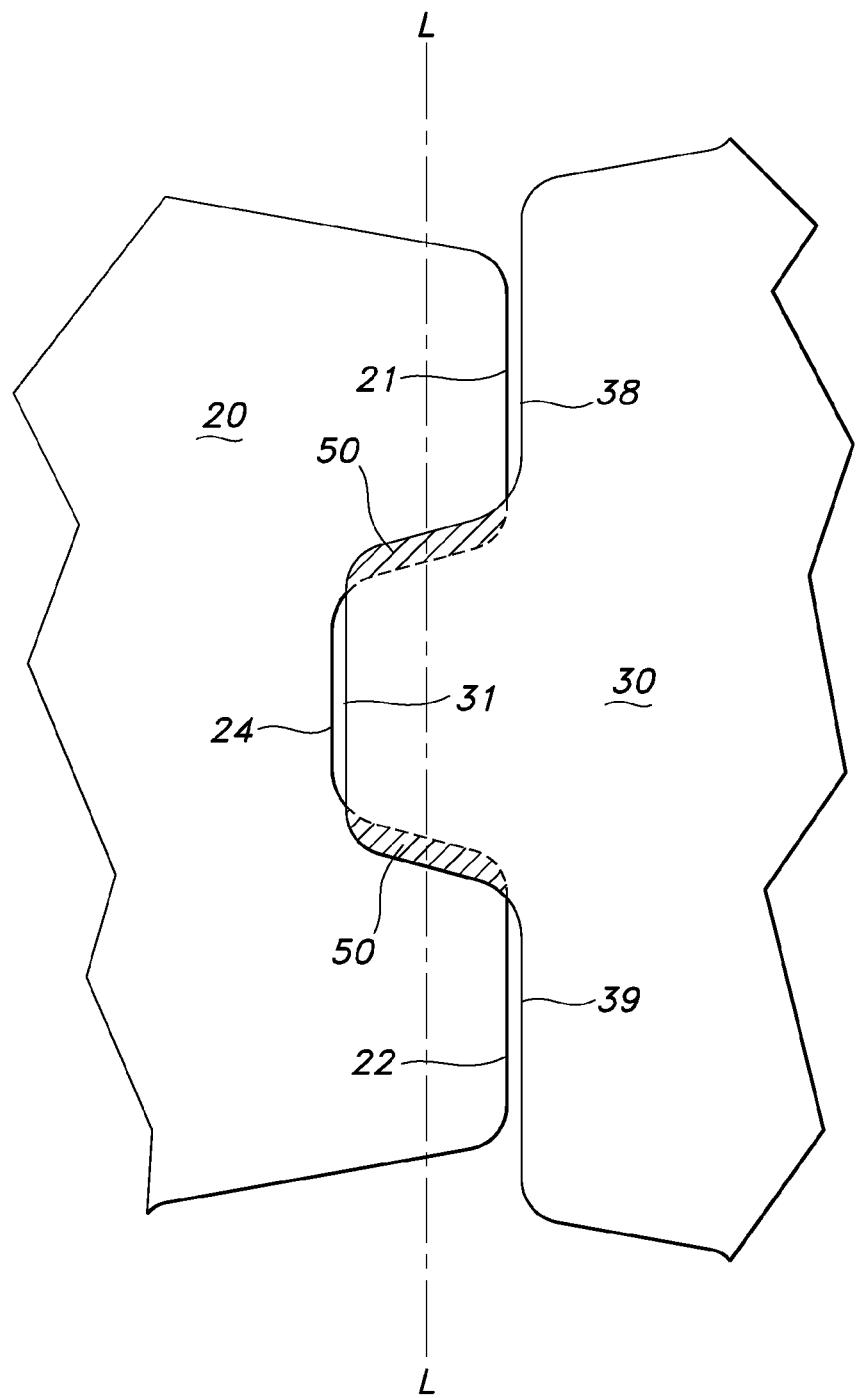

In a further embodiment, and in reference to FIGS. 4 and 5, the first and second wings 20, 30 are sized and shaped so that the wings form overlap regions 50 when folded around the underside of the article 10 and extended to lay flat against the backsheet 14. Thus, in use, the first wing 20 and second wing 30 can extend around the crotch portion of the garment and the first peak 31 of the second wing 30 extends over the furrow base 24 of the first wing 20 in an overlapping relationship. In this embodiment the wings are sized and shaped so as to inter-mesh in a manner such that the wings superpose one another. When the wings 20, 30 are folded around the underside of the article 10 so as to lay flat against the backsheet 14, individual overlap regions 50 formed by the superposed portions of the first wing 20 and second wing 30 desirably each comprise an area of at least about 50 mm$^2$, more desirably between about 50-600 mm$^2$ and still more desirably between about 100-250 mm$^2$. In a particular embodiment and in reference to FIG. 4, the dimension of the wings relative to the width of the article 10 (exclusive of the wings) is such that the first and second wings 20, 30 form overlap regions 50 adjacent the outer edges of the peaks 21, 22 and 31 extending generally in the longitudinal direction. In a further particular embodiment and in reference to FIG. 5, the shape and dimension of the wings 20, 30 relative to the width of the article 10 (exclusive of the wings) is such that the first and second wings 20, 30 form overlap regions 50 adjacent the side edges of the peaks 21, 22 and 31 extending generally in the transverse direction T. The wings 20, 30 can include fasteners (not shown) positioned on one or both areas of the wings intended to overlap and directly engage one another. Desirably the fasteners are positioned adjacent the edges of the peaks 21, 22, 31. The wings may optionally include secondary fasteners such as pressure sensitive adhesive located in one or more areas of the wings 20, 30 intended to overly the garment when worn.

Figure 6:
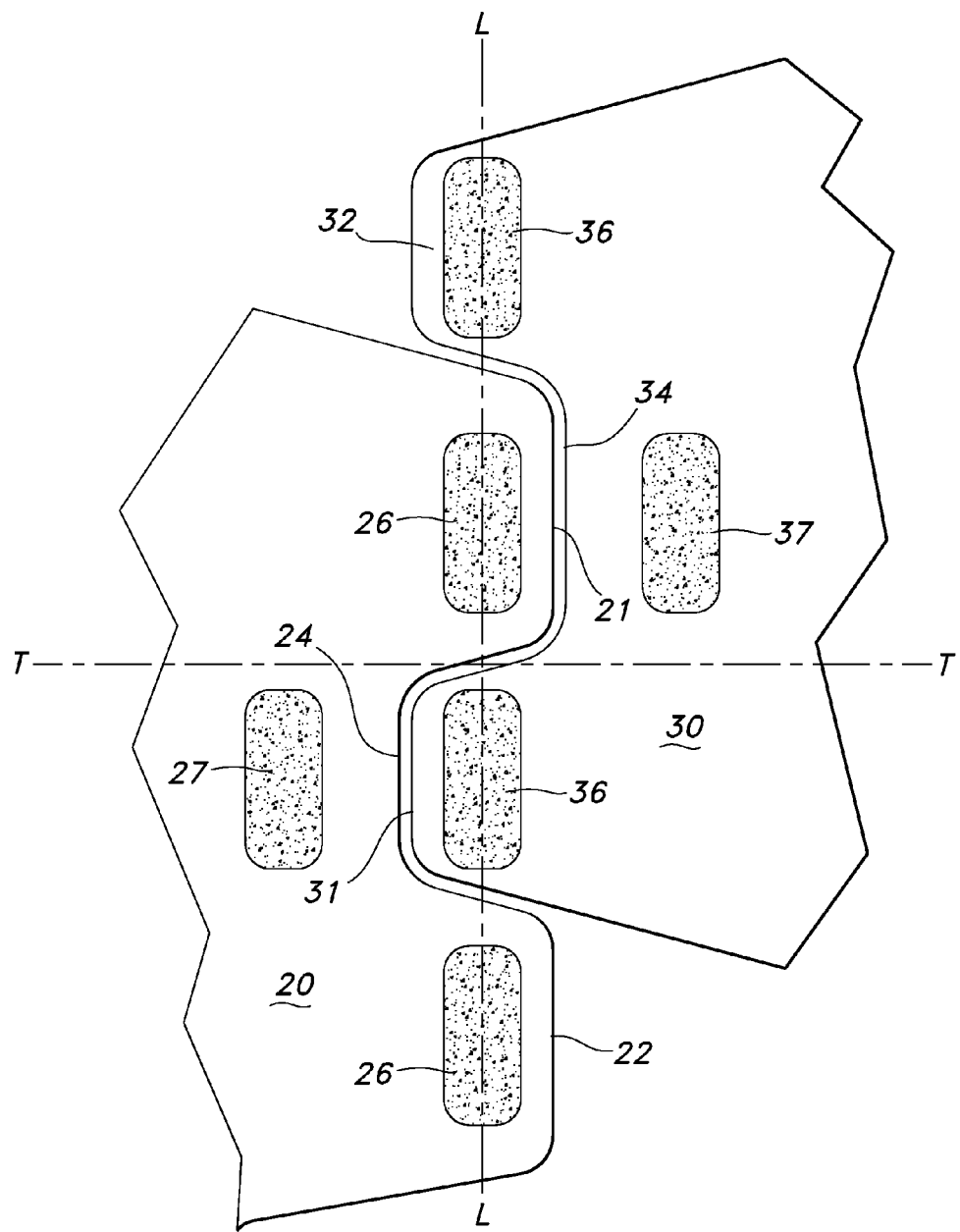

In still a further embodiment and in reference to FIG. 6, the second wing 30 can have a shape the same as or substantially similar to that of the first wing 20. Thus, in this embodiment, the first wing 20 and second wing 30 each have first peaks 21, 31, second peaks 22, 32 and furrow bases 24, 34 respectively. The first peaks 21, 31 and second peaks 22, 32 are sized so as to extend beyond the longitudinal centerline "L" when the wings 20, 30 are folded under the backside of the article and extended so as to lay flat against the backsheet 14. In addition, the wings 20, 30 are off-set from one another such that, when the wings are folded around the underside of the article and extended so that the wings 20, 30 lay flat against the backsheet 14, the first peak 31 of the second flap 30 extends into the furrow of the first wing 20 and the first peak 21 of the first wing 20 extends into the furrow of the second wing 30. As will be readily understood by one skilled in the art, the multiple peaks of the wings can be configured to have non-overlapping relationships, overlapping relationships or both an overlapping and non-overlapping relationship. Accordingly, the wings will contain a plurality of fasteners in accord with the selected overlap scheme and fastening mechanism. In reference to FIG. 6, the primary fasteners 26, 36 traverse the longitudinal centerline "L."

The front and rear halves of each wing can be symmetrical or asymmetrical as desired. For example, in one embodiment and in reference to FIG. 1, the front and rear halves of the wings, i.e. the halves above and below the transverse centerline in the longitudinal direction, are symmetrical. The absorbent core in the embodiment of FIG. 1 is also symmetrical and commonly it will be desirable for the wings to be symmetrical when the absorbent core is symmetrical. In an alternate embodiment, and in reference to FIG. 2, the absorbent core 16 is shaped having wider front (F) and narrower rear (R) sections in order to better conform to a tanga or thong type undergarments as well as for use in connection with certain overnight pads. The wings are therefore configured to correspond with the difference in the width of the article 10. More specifically, the first peak 21 of first wing 20, which is positioned adjacent a wider section of the absorbent core 16, has a greater dimension in the transverse direction than the rearward second peak 22 of the first wing 20. In the embodiment shown in FIG. 2 the wings 20, 30 are centered about the transverse centerline "T" of the article however, as noted previously, the wings 20, 30 can be positioned either forwardly or rearwardly relative to the transverse centerline as desired.

With respect to the general function and composition of the article 10, the backsheet or outer cover 12 functions to isolate absorbed fluids from the wearer's garments and therefore comprises a liquid-impervious material. In one aspect the outer cover may optionally comprise a material that prevents the passage of liquids but allows air and water-vapor to pass there through. The outer cover can comprise a single layer or multiple layers and these one or more layers can themselves comprise similar or different materials. Suitable backsheet materials include, but are not limited to, polyolefin films, nonwovens and film/nonwoven laminates. The particular structure and composition of the outer cover may be selected from various known films and/or fabrics with the particular material being selected as appropriate to provide the desired level of liquid barrier, strength, abrasion resistance, tactile properties, aesthetics and so forth. Suitable outer covers include, but are not limited to, those described in U.S. Pat. No. 4,578,069 to Whitehead et al.; U.S. Pat. No. 4,376,799 to Tusim et al.; U.S. Pat. No. 5,695,849 to Shawver et al; U.S. Pat. No. 6,075,179 et al. to McCormack et al. and U.S. Pat. No. 6,376,095 to Cheung et al.

The topsheet 14 functions to receive and take in fluids, such as urine or menses, and therefore comprises a liquid permeable material. Additionally, topsheets can further function to help isolate the wearer's skin from fluids held in the absorbent core 16. Topsheets can comprise a single layer or multiple layers and these one or more layers can themselves comprise similar or different materials. Topsheets are well known in the art and may be manufactured from a wide variety of materials such as, for example, porous foams, reticulated foams, apertured plastic films, woven materials, nonwoven webs, aperture nonwoven webs and laminates thereof. It is also well known that one or more chemical treatments can be applied to the topsheet materials in order to improve movement of the fluid through the topsheet and into the article. Suitable topsheets include, but not limited to, those described in U.S. Pat. No. 4,397,644 to Matthews et al.; U.S. Pat. No. 4,629,643 to Curro et al.; U.S. Pat. No. 5,188,625 Van Iten et al.; U.S. Pat. No. 5,382,400 to Pike et al.; U.S. Pat. No. 5,533,991 to Kirby et al.; and U.S. Pat. No. 6,410,823 to Daley et al. Between the liquid pervious topsheet 12 and liquid impervious backsheet 14 is positioned an absorbent core 16. The absorbent core 16 functions to absorb and preferably "lock-up" the bodily fluids that pass into the absorbent article 10 through the topsheet 12. The absorbent core can comprise a single layer or multiple layers and these one or more layers can themselves comprise similar or different materials. In order to efficiently and effectively utilize the absorbent capacity of the article, it is common for the absorbent core to include one or more liquid distribution layers or wicking layers in combination with a highly absorbent layer that preferentially absorbs and retains the liquids. Suitable wicking layers include, but are not limited to, bonded-carded webs, hydroentangled nonwoven webs, or spunbond webs containing fibers treated with or containing one or more topical agents that improve the contact angle with the bodily fluid and/or modify the flow properties of the bodily fluid. Highly absorbent layers often include, but not limited to, batts or webs containing wood pulp fibers, superabsorbent particles, synthetic wood pulp fibers, synthetic fibers and combinations thereof. The absorbent core may comprise any one of a number of materials and structures, the particular selection of which will vary with the desired loading capacity, flexibility, body fluid to be absorbed and other factors known to those skilled in the art. By way of example, suitable materials and/or structures for the absorbent core include, but are not limited to, those described in U.S. Pat. No. 4,610,678 to Weisman et al.; U.S. Pat. No. 6,060,636 to Yahiaoui et al.; U.S. Pat. No. 6,610,903 to Latimer et al.; US20100174260 to Di Luccio et al.; and U.S. Pat. No. 7,358,282 to Krueger t al.

The shape of the absorbent core can vary as desired and can comprise any one of various shapes including, but not limited to, generally triangular, rectangular, dog-bone and elliptical shapes. In one embodiment, the absorbent core 16 has a shape that generally corresponds with the overall shape of the article 10 such that the absorbent core terminates proximate the edge seal 18 and wings 20, 30. The dimensions of the absorbent core can be substantially similar to those referenced above with respect to the absorbent article 10; however it will be appreciated that the dimensions of the absorbent core 16 while similar will often be slightly less than those of the overall absorbent article 10 in order to be contained therein.

As previously indicated, the absorbent core 16 is positioned between the topsheet 12 and backsheet 14. The individual layers comprising the article can be attached to one another using means known in the art such as adhesive, heat/pressure bonding, ultrasonic bonding and other suitable mechanical attachments. Commercially available construction adhesives usable in the present invention include, for example Rextac adhesives available from Huntsman Polymers of Houston, Tex., as well as adhesives available from Bostik Findley, Inc., of Wauwatosa, Wis. In one embodiment, and in reference to FIG. 1, the absorbent core can be sealed between the topsheet 12 and backsheet 14 along the perimeter of the absorbent core 16 along edge seal 18 formed by the application of heat and pressure to melt thermoplastic polymers located in the topsheet 12 and/or backsheet 14.

The wings can be constructed from materials described above with respect to the topsheet and backsheet. In one embodiment, the wings can comprise an extension of a layer of material within the topsheet and/or backsheet. By way of example and in reference to FIG. 1, the wings 20, 30 can be formed by an extension of the topsheet 12 and backsheet 14 that are welded together along edge seal 18. Such wings can be integrally formed with the main portion of the absorbent article. Alternatively, the wings can be formed independently and separately attached to an intermediate section of the article. Wings that are made independent of the other components of the absorbent article can be welded onto or adhesively joined to a portion of the topsheet and/or backsheet. In addition, as is known in the art, when cutting materials to the desired shape it is preferable to arrange the components so as to minimize waste. Examples of processes for manufacturing absorbent articles and wings include, but are not limited to those described in U.S. Pat. No. 4,059,114 to Richards; U.S. Pat. No. 4,862,574 to Seidy et al. WO1997040804 to Emenaker et al.; U.S. Pat. No. 5,342,647 to Heindel et al.; US20040040650 to Venturino et al.; and U.S. Pat. No. 7,070,672 to Alcantara et al.

In order to further assist with the maintenance of the article 10 in the desired location on the undergarment, garment adhesive (not shown) may be applied to the garment facing side of the backsheet 14. The use of garment adhesive on the backsheet to help secure placement of an absorbent article on the garment is well known in the art and there are numerous adhesive patterns and releasable peel strips suitable for use with the present invention. Examples of suitable garment adhesives, patterns and release sheets include, but are not limited to, those described in DE700225U1; U.S. Pat. No. 3,881,490 to Whitehead et al.; U.S. Pat. No. 3,913,580 Ginocchio; U.S. Pat. No. 4,337,772 to Roeder et al.; GB1349962 Roeder; U.S. Pat. No. 4,556,146 to Swanson et al.; and US20070073255A1 to Thomas et al.

The absorbent articles of the present invention may further include one or more components or elements as may be desired. By way of example, the absorbent article may optionally include slits, voids or embossing on the topsheet and/or absorbent core in order to improve fluid intake, fluid distribution, stiffness (bending resistance) and/or aesthetic appeal. As a specific example and in reference to FIGS. 1 and 6, embossing 17 can extend into both the topsheet 12 and absorbent core 16. Examples of additional suitable embossing patterns and methods include, but are not limited to, those are described in U.S. Pat. No. 4,781,710 Megison et al.; EP769284A1 to Mizutani et al.; US20050182374 to Zander et al.; and U.S. Pat. No. 7,686,790 to Rasmussen et al.

The personal care articles can, optionally, contain one or more additional elements or components as are known and used in the art including, but not limited to, the use of fold lines, individual wrappers, elasticated flaps that extend above the plain of the topsheet in use, additional independent wings such as about the ends, odor control agents, perfumes, and the use of ink printing on one or more surfaces of the topsheet, backsheet, wings or absorbent core. Still further additional features and various constructions are known in the art. Thus, while the invention has been described in detail with respect to specific embodiments and/or examples thereof, it will be apparent to those skilled in the art that various alterations, modifications and other changes may be made to the invention without departing from the spirit and scope of the same. It is therefore intended that the claims cover or encompass all such modifications, alterations and/or changes.

What is claimed is:

1. An absorbent personal care article comprising:
a wearer-facing side and a garment-facing side;
an elongate shape defined by opposed first and second sides extending in a longitudinal direction and opposed front and rear ends extending in a transverse direction, said article having a longitudinal centerline;
a liquid permeable topsheet, a liquid impermeable backsheet and an absorbent core disposed between the liquid permeable topsheet and liquid impermeable backsheet;
a first flap extending from the first side and having first and second peaks and a furrow positioned between said first and second peaks;
a second flap extending from the second side and having a first peak;
a fastener positioned on the garment facing side of at least one of the first and second flaps;
wherein the first flap and the second flap are sized such that, when folded under the article and extended to lay flat against the liquid impermeable backsheet, the first peak of the second flap extends across the longitudinal centerline of the article and into the furrow of the first flap.

2. The absorbent personal care article of claim 1 wherein the furrow of the first flap and the first peak of the second flap are sized and shaped to substantially conform with one another when the first and second flaps are folded under the article and extended to lay flat against the liquid impermeable backsheet.

3. The absorbent personal care article of claim 2 wherein, when folded under the article and extended to lay flat against the liquid impermeable backsheet, the first flap and the second flap do not overlap thereby forming a gap between the first and second flaps.

4. The absorbent personal care article of claim 3 wherein the gap between the first flap and second flap is less than 15 mm when the first and second flaps are folded under the article and extended to lay flat against the liquid impermeable backsheet.

5. The absorbent personal care article of claim 4 wherein the gap between the first flap and second flap is substantially uniform when the first and second flaps are folded under the article and extended to lay flat against the liquid impermeable backsheet.

6. The absorbent personal care article of claim 1 wherein fasteners are positioned each of on the peaks of the first and second flaps whereby the fasteners extend across the longitudinal centerline of the article when the first and second flaps are folded under the article and extended to lay flat against the liquid impermeable backsheet.

7. The absorbent personal care article of claim 6 wherein the fasteners comprise an adhesive and are located proximate to outer edges of the peaks.

8. The absorbent personal care article of claim 7 wherein, when the first and second flaps are folded under the article and extended to lay flat against the liquid impermeable backsheet, the fasteners lie entirely opposite the longitudinal centerline of the article relative to the side that the respective wing is attached.

9. The absorbent personal care article of claim 1 wherein, when folded under the article and extended to lay flat against the liquid impermeable backsheet, the first flap and the second flap overlap and have an area of overlap of at least 50 mm$^2$.

10. The absorbent personal care article of claim 1 wherein the fastener is located on at least one of the first or second flaps such that, when the first and second flaps are folded under and adjacent the liquid impermeable backsheet, the first flap and the second flap overlap and the fastener releasably joins superposed portions of the first and second flaps.

11. The absorbent personal care article of claim 10 wherein the first peak of the second flap overlaps a base of the furrow of the first flap when the first and second flaps are folded under the article and extended to lay flat against the liquid impermeable backsheet.

12. The absorbent personal care article of claim 11 wherein the second flap has shoulders adjacent the first peak and further wherein the first peak of the first flap overlaps the shoulder of the second flap when the first and second flaps are folded under and adjacent the liquid impermeable backsheet.

13. The absorbent personal care article of claim 10 wherein, when the first and second flaps are folded under the article and extended to lay flat against the liquid impermeable backsheet, an intermediate portion of the first peak of the first flap overlaps an intermediate portion of the first peak of the second flap thereby forming an overlap region generally extending in the transverse direction.

14. The absorbent personal care article of claim 1 wherein the first and second flaps extend between about 20-70% of the length of the article.

15. The absorbent personal care article of claim 14 wherein the longitudinal distance from the middle of the first peak of the first flap to the middle of the furrow of the first flap peak is between about 20 and about 60 mm.

16. The absorbent personal care article of claim 15 wherein the first and second flaps are centered about a transverse center line of the article.

17. The absorbent personal care article of claim 1 wherein:
the absorbent core has an asymmetrical shape having a front end having a greater width than the rear end of the article; and
further wherein the first peak of the first flap is positioned forward of the second peak of the first flap; and
further wherein the first peak of the first flap extends a greater distance from the longitudinal centerline than the second peak of the first flap.

18. The absorbent article of claim 17 wherein the absorbent core has a generally triangular shape.

19. The absorbent personal care article of claim 1 wherein the second flap further includes a second peak and a furrow positioned between the first and second peaks and further wherein the first flap and second flap are sized and positioned such that, when folded under the article and extended to lay flat against liquid impermeable backsheet, the second peak of the first flap extends into the furrow of the second flap.

20. The absorbent personal care article of claim 1 wherein the first and second flaps are independently formed from the topsheet and backsheet and are joined to at least one of the topsheet or backsheet.

* * * * *